United States Patent [19]
Frazier et al.

[11] Patent Number: 6,136,171
[45] Date of Patent: Oct. 24, 2000

[54] MICROMACHINED ELECTRICAL FIELD-FLOW FRACTIONATION SYSTEM

[75] Inventors: A. Bruno Frazier, Salt Lake City, Utah; Karin D. Caldwell, Uppsala, Sweden; Bruce K. Gale, Murray, Utah

[73] Assignee: The University of Utah Research Foundation, Salt Lake City, Utah

[21] Appl. No.: 09/156,151

[22] Filed: Sep. 18, 1998

[51] Int. Cl.[7] .......................... G01N 27/26; G01N 27/447
[52] U.S. Cl. .......................... 204/450; 204/547; 204/600; 204/643; 209/127.1; 209/129
[58] Field of Search .................... 204/450, 547, 204/600, 643; 209/127.1, 129

[56] References Cited

U.S. PATENT DOCUMENTS

| | | | |
|---|---|---|---|
| 3,449,938 | 6/1969 | Giddings | 73/23.39 |
| 3,811,841 | 5/1974 | Kassel | 422/82 |
| 4,147,621 | 4/1979 | Giddings | 210/637 |
| 4,250,026 | 2/1981 | Giddings et al. | 209/155 |
| 4,420,720 | 12/1983 | Newton et al. | 324/71.4 |
| 4,446,015 | 5/1984 | Kirkland | 209/155 |
| 4,737,268 | 4/1988 | Giddings | 209/12 |
| 4,830,756 | 5/1989 | Giddings | 210/239 |
| 4,908,112 | 3/1990 | Pace | 204/601 X |
| 5,023,054 | 6/1991 | Sato et al. | 422/82.09 |

(List continued on next page.)

OTHER PUBLICATIONS

David W. Shortt et al, "Absolute Measurement of Diameter Distributions of Particles Using a Multiangle Light Scattering Photometer Coupled With Flow Field Flow Fractionation" American Laboratory, vol. 28(17)pp. 21–28, Nov. 1996.

Christoph Johann, "Field–flow Fractionation (FFF) for the Characterization of Polymers and Particles" CLB Chemie in Labor und Biotechnik, vol. 47(8) pp. 355–357, 1996.

Gale et al, "Micromachined Electrical Field–Flow Fractionation ($\mu$–EFFF) System" IEEE Micro Electro Mechanical Systems Conference, Nagoya, Japan, Jan. 26–30, 1997.

Takashima et al., Frequency Domain Studies of Impedance Characteristics of Biological Cells Using Micropipet Technique, Biophysical Journal, vol. 54, pp. 995–1000, Dec. 1988.

Bao et al., Impedance Spectroscopy of Human Erythrocytes: System Calibration and Nonlinear Modeling, IEEE Transactions on Biomedical Engineering, vol. 40, No. 4, pp. 364–378, Apr. 1993.

(List continued on next page.)

*Primary Examiner*—Jill Warden
*Assistant Examiner*—John S. Starsiak, Jr.
*Attorney, Agent, or Firm*—Workman, Nydegger & Seeley

[57] ABSTRACT

A micromachined system for electrical field-flow fractionation of small test fluid samples is provided. The system includes a microchannel device comprising a first substrate having a planar inner surface with an electrode formed thereon. A second substrate having a planar inner surface with an electrode formed thereon is positioned over the first substrate so that the respective electrodes face each other. An insulating intermediate layer is interposed between the first and second substrates. The intermediate layer is patterned to form opposing sidewalls of at least one microchannel, with the electrodes on the substrates defining opposing continuous boundaries along the length of the microchannel. Inlet and outlet ports are formed in one or both substrates for allowing fluid flow into and out of the microchannel. The microchannel device can be fabricated with single or multiple microchannels therein for processing single or multiple test fluids. During operation, a voltage differential is applied to the electrodes in order to induce an electric field across the microchannel. This separates particles of different types present in a fluid injected into the microchannel. The separated particles in the fluid can be collected or further processed as desired.

56 Claims, 9 Drawing Sheets

U.S. PATENT DOCUMENTS

| | | | |
|---|---|---|---|
| 5,144,224 | 9/1992 | Larsen | 324/71.4 |
| 5,240,618 | 8/1993 | Caldwell et al. | 210/748 |
| 5,464,581 | 11/1995 | van den Engh | 422/82.01 |
| 5,489,506 | 2/1996 | Crane | 435/2 |
| 5,605,662 | 2/1997 | Heller et al. | 422/68.1 |
| 5,632,957 | 5/1997 | Heller et al. | 422/68.1 |
| 5,871,158 | 2/1999 | Frazier | 239/548 |
| 5,876,582 | 3/1999 | Frazier | 205/122 |

OTHER PUBLICATIONS

Lo et al., Impedance Analysis of MDCK Cells Measured by Electric Cell–Substrate Impedance Sensing, Biophysical Journal, vol. 69, pp. 2800–2807, Dec. 1995.

Gimsa et al., Dielectric Spectroscopy of Single Human Erythrocytes at Physiological Ionic Strength: Dispersion of the Cytoplasm, Biophysical Journal, vol. 71 pp. 495–506, Jul. 1996.

Gale et al., Micromachined Electrical Field–Flow Fractionation ($\mu$–EFFF) System, IEEE Micro Electro Mechanical Systems Conference, Nagoya, Japan, Jan. 26–30, 1997.

Ayliffe et al., Micromachined Cellular Characterization System for Studying the Biomechanics of Individual Cells, 1997 International Conference on Solid–State Sensors and Actuators, Chicago, pp. 1307–1310, Jun. 16–19, 1997.

MICROMACHINED ELECTRICAL FIELD-FLOW FRACTIONATION SYSTEM

The U.S. Government has a paid-up license in this invention and the right in limited circumstances to require the patent owner to license others on reasonable terms as provided for by the terms of Grant No. NSF DB19730991 awarded by the National Science Foundation.

BACKGROUND OF THE INVENTION

1. The Field of the Invention

The present invention relates to a system and method for the separation of biological and chemical materials which are in a liquid solution. More particularly, the present invention relates to a micromachined system for separation of molecules and particulate materials which utilizes electrical field-flow fractionation techniques.

2. The Relevant Technology

Field flow fractionation techniques are commonly used to perform separation and analysis of molecules and large molecular complexes which are in solution form. In theory, several different mechanisms can be employed to separate particles of differing varieties from a fluid stream; an example being separation by differences in mass or electrochemical potential through the application of an appropriate "driving" force. This driving force can be used to induce a displacement of a particular species in a certain direction such as towards what is commonly termed the "accumulation wall." From a practical point of view, a particularly convenient means of separation can be achieved through the application of an electric field, since electric fields are easily applied, controlled, and monitored in a typical laboratory setting. Therefore, the electric field is generally accepted as being one of the preferred methods to achieve separation of particles in solution form when accurate quantitative results are required.

In many applications, and particularly in biotechnology, there is a great demand for fast separation systems which have an adequate degree of resolution. Various methods have been proposed to achieve the separation of particles such as polymers, cells, and viruses. The majority of these methods, however, have various difficulties which include being too slow, too complicated, low in throughput, low in resolution, and too expensive to be practical for commercial and industrial applications.

Other techniques exist for the separation of both small molecules and also larger complexes of molecules, such as organelles and cells, which are in solute form. For example, molecular separations can be performed with high yield by ion exchange or reverse phase chromatography, which are methods that use chemicals to achieve separation. Chemical separations are observed, however, to have the undesirable effect of denaturing proteins, and are therefore unsuitable for certain applications. Centrifugation can be used to separate cells and organelles, although this technique often fails to resolve different types of cells due to similarities in cell densities. Molecular separation can also be done by electrophoresis, which separates samples by variation in molecular size. Typical electrophoresis systems require very high field strengths, which can result in the unwanted formation of electrolysis by-products in the vicinity of the electrodes. Conventional electrophoresis systems also employ a vertically oriented channel through which the sample containing the fluid must flow, which can result in the disadvantage of distortion in laminar flow conditions due to the effects of gravity.

In contrast with electrophoresis separation systems, electric field flow fractionation (EFFF) techniques utilize an electric field which is applied perpendicular to the direction of flow, and achieve separation by distinguishing amongst particles which flow at different velocities through a thin, horizontally oriented (with respect to the gravitational field) channel. The difference in velocities of various particles in the liquid arises from differences in the size and charge of each particle, quantities which are characterized together in a parameter which has been termed as the "$\zeta$ potential." The $\zeta$ potential of a particle is a useful parameter in that it may be considered to be a measure of its effective charge.

In EFFF techniques, the electrodes are placed on the top and bottom of the thin channel, allowing for the application of the electric field in a direction perpendicular to the flow. The EFFF process is based on a distinction amongst the differing velocities of the particles, and the forcing of particles with higher $\zeta$ potential towards the accumulation wall of the channel, while particles with lower $\zeta$ potential remain in the middle of the stream. As the various particles flow through the channel under the influence of the electric field, particles of differing $\zeta$ potentials and sizes will flow at different rates. The final equilibrium position of a species is determined by the combined effect of parameters such as the magnitude of the applied voltage and its polarity, the channel dimensions, and the viscosity of the flow medium. Various species of different sizes and different charges will thus be separated in accordance with their $\zeta$ potentials along different locations in the flow channel.

For the fluid velocities and channel dimensions utilized in EFFF systems, the Reynolds number is less than one. For this case, the flow in such a channel may be considered to be laminar. Laminar flow conditions imply that the velocity of the fluid flow is greater near the center of the channel and that the velocity is slowest near the walls of the channel, and hence may be well approximated by a substantially parabolic profile with respect to the velocity as a function of lateral position in the channel.

The EFFF techniques have all of the advantages of electrophoretic separation systems, but in addition, can satisfactorily perform separation of cells, large molecules, colloids, emulsions, and delicate structures such as liposomes, which cannot be accomplished by conventional electrophoretic systems. Possible applications where EFFF systems can supersede or complement electrophoretic separation systems include sample purification, cell separations, characterizations of emulsions, separations of particulates for intravenous drug administration, diagnostic tests for specific molecules in colloidal suspensions, and research into various aspects of $\zeta$ potentials.

Various field flow fractionation systems have been developed in the past, such as that disclosed in U.S. Pat. No. 4,737,268 to Giddings. The system in Giddings' patent specifies a thin channel in which the fluid containing the particles to be separated flows in a laminar fashion under the application of a field or field gradient applied transversely to the direction of flow, in order to separate the various particles into different stream laminae. The flow rate is adjusted in such a way as to ensure laminar flow conditions and under the influence of the field or field gradient, the different species of particles will approach different transverse equilibrium distributions. The system also includes a splitting means to separate and recover the substreams which contain the various types of particles.

Another innovation in the area of electric field flow fractionation is disclosed in U.S. Pat. No. 5,240,618 to Caldwell et al., which describes an apparatus including a thin flow channel having top and bottom walls that are formed such that the inner surfaces thereof are made of an electrically conductive material to function as electrodes. The carrier fluid flowing through the channel can be water containing a red-ox couple such as quinone/hydroquinone to reduce polarization effects.

The last several years have seen tremendous development in the area of fabrication techniques for small (on the order of a micron) sized separation systems. This has been made possible by the progress in techniques utilized in the everyday fabrication of integrated circuits and semiconductor microsensors. The fabrication technologies utilized therein are commonly referred to as "micromachining" methods. A number of electrophoresis systems have been previously constructed by micromachining techniques, which typically include steps such as chemical etching of semiconductor wafers, thin film deposition, lithographic patterning, etc.

In U.S. Pat. No. 4,908,112 to Pace, a micromachined analytical separation device is disclosed in which a capillary sized conduit is formed by a channel in a semiconductor device, with the channel closed by a glass plate. A series of electrodes are positioned in the channel which are used to activate the motion of liquids flowing through the conduit.

Prior micromachined EFFF systems have typically utilized materials including titanium, gold, and certain plastics which have previously been demonstrated to be biocompatible. However, the plastics which have been hitherto implemented have been the source of complications in the fabrication steps.

It would therefore be of substantial interest to develop a system which is capable of separating small samples with enhanced resolution, and which overcomes the difficulties associated with prior systems.

SUMMARY AND OBJECTS OF THE INVENTION

It is a primary object of the present invention to provide a microchannel device for an electrical field-flow fractionation system which can separate various species of molecules or particulates in solution with enhanced resolution.

It is a further object of the invention to provide a microsized electrical field-flow fractionation system which can perform the separation of various molecules or particulates in solution with very small sample sizes efficiently, quickly, and inexpensively, and with a high degree of resolution.

It is yet another object of the invention to provide a method of fabricating a microchannel device by micromachining techniques which allows simple and precise construction of the microchannels.

An additional object of the present invention is to provide a method of fabricating a microchannel device with biocompatible materials.

To achieve the foregoing objects, and in accordance with the invention as embodied and broadly described herein, a micromachined system for electrical field-flow fractionation of small test fluid samples is, provided. The system includes a microchannel device comprising a first substrate having a planar inner surface with an electrically conductive layer such as an electrode formed thereon. The system also includes a second substrate having a planar inner surface with an electrically conductive layer such as an electrode formed thereon. The second substrate is positioned over the first substrate so that the respective conductive layers of the first and second substrates face each other. An intermediate layer such as an insulating layer is interposed between the first and second substrates, with the intermediate layer being patterned to form opposing sidewalls of at least one microchannel. The conductive layers on the first and second substrates define opposing continuous boundaries along the length of the microchannel. Inlet and outlet ports are formed in the first and/or second substrate to allow fluid flow into and out of the microchannel.

The microchannel device can be fabricated by conventional micromachining techniques with single or multiple microchannels therein for processing single or multiple test fluids. When a microchannel device is formed with a plurality of microchannels therein, a plurality of electrodes are formed on the substrates such that each microchannel is bounded by opposing electrode strips. In addition, a plurality of inlet and outlet ports are formed in the substrates for allowing fluid flow into and out of each microchannel.

The microchannel device of the invention is connected to other conventional apparatus in order to form a fully functional system for the separation of molecules or particulates in solution. For example, each inlet port of the microchannel device can be in fluid communication with a buffer reservoir, a pump, a sample input device, and a flow rate controller. The outlet port can be in fluid communication with a fraction collector. Each microchannel is also operatively connected to a detector, which can be on-chip with the device or off-chip.

Alternative system embodiments of the present invention utilize a plurality of microchannels for parallel or serial analysis of sample fluids. A parallel analysis system of the invention includes a plurality of microchannels, which can be implemented utilizing separate microchannel devices each with one microchannel therein or with a microchannel device having multiple microchannels therein, for multiple simultaneous processing of sample fluids. A serial analysis system of the invention includes a plurality of microchannel devices, which are interconnected serially, allowing stepwise processing of a sample fluid in a purification scheme.

During operation of the system of the invention, a voltage differential is applied to the electrodes on the substrates in order to induce an electric field across the microchannel. A test fluid is injected through the inlet port and into the microchannel, and the fluid is passed through the microchannel with the electric field therein in order to separate particles of different types in the fluid. The separated particles in the microchannel are monitored by the detector, and the fluid can be subsequently collected or further processed as desired.

The system of the present invention allows greater resolution in the separation of various particles such as different molecular species, and permits smaller sample sizes to be analyzed at faster rates than what has been achieved in prior systems.

These and other aspects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE INVENTION

Figure 1:
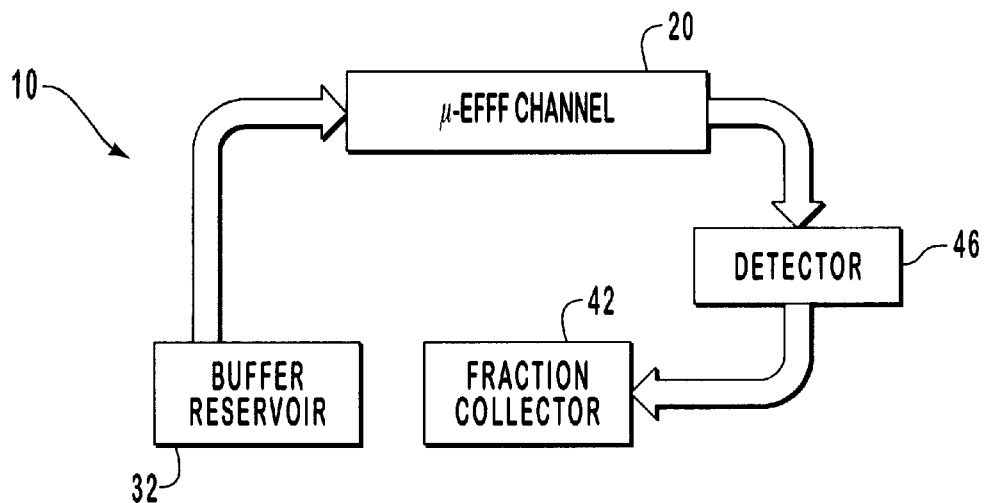
FIG. 1 is a schematic depiction of a micro electrical field-flow fractionation ($\mu$-EFFF) system according to one embodiment of the present invention.

The present invention is directed to a micro electric field flow fractionation ($\mu$-EFFF) system for the separation of various types of molecules or particulates in solution. The $\mu$-EFFF system utilizes a microchannel device fabricated by micromachining techniques from biocompatible materials. As used herein, the term "micromachining" refers to techniques which are used in the electronics and microsensor fabrication industries, and includes the processes of semiconductor etching, thin film deposition, lithographic patterning, and the like.

The microchannel device allows the $\mu$-EFFF system of the invention to be capable of high resolution analysis of very small (micro-sized) liquid samples. In one preferred embodiment of the present invention, the microchannel device is formed on a silicon wafer by micromachining techniques.

Referring to the drawings, wherein like structures are provided with like reference designations, the drawings only show the structures necessary to understand the present invention. Additional structures known in the art have not been included to maintain the clarity of the drawings.

FIG. 1 is a schematic depiction of a $\mu$-EFFF system 10 according to the present invention. The system 10 generally includes a microchannel 20 which is in fluid communication at an input end thereof with a reservoir 32 and associated flow control and input devices. The microchannel 20 can also be in fluid communication at an output end thereof with a fraction collector 42, and is operatively connected to a detector 46. Each of these components of system 10 will be discussed in further detail below.

Figure 2:
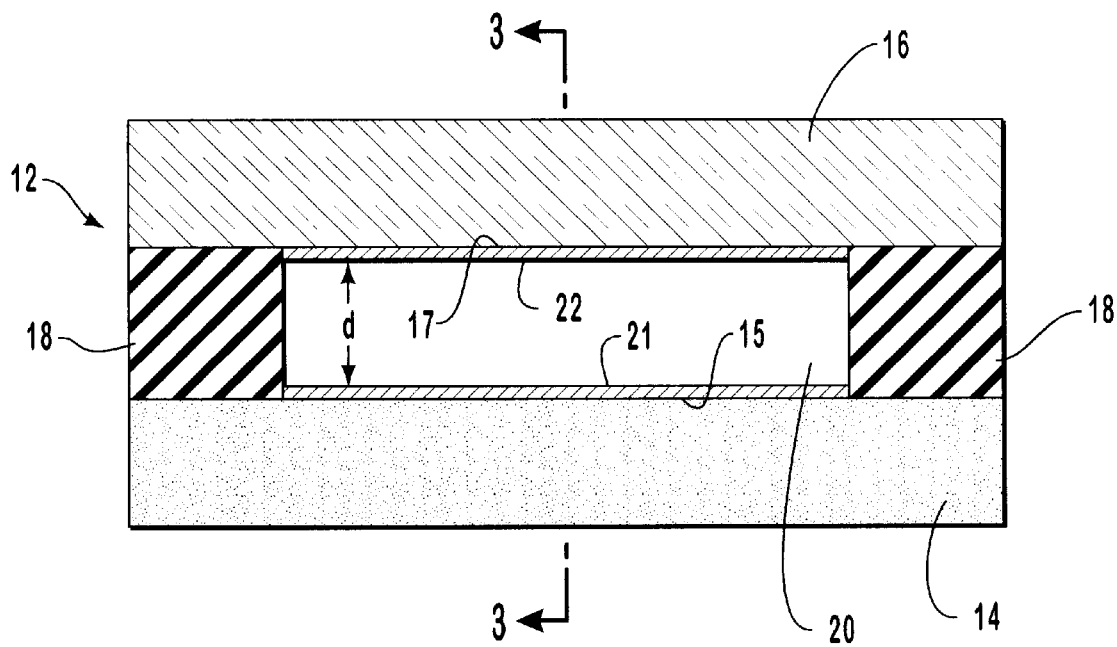
FIG. 2 is a schematic cross-sectional view perpendicular to fluid flow of a microchannel device for use in a $\mu$-EFFF system of the present invention.

A microchannel device 12 defining microchannel 20 is shown in FIG. 2 in a schematic cross-sectional view perpendicular to the flow. The microchannel device 12 includes a first substrate 14 having a substantially planar inner surface 15. The substrate 14 can be composed of a variety of materials including metallic materials, semiconductor materials such as silicon, nonconductive materials such as glass, plastic materials, and various composites or combinations thereof. A second substrate 16 is positioned over substrate 14 and is supported by sidewalls 18 which are discussed in further detail below. The substrate 16 has a substantially planar inner surface 17 and can be composed of a variety of materials such as those discussed above for substrate 14, including metals, silicon, glass, plastic materials, and the like. The substrates 14 and 16 can be composed of the same or different materials. For example, in one embodiment of the invention, substrate 14 is composed of a semiconductor material such as silicon and substrate 16 is composed of a nonconductive material such as glass.

The sidewalls 18 are formed from an intermediate layer deposited on substrate 14 and patterned at selected locations to form opposing sidewalls 18 defining at least one microchannel 20. The intermediate layer forming sidewalls 18 is preferably an insulating material which can be selected from various biocompatible materials such as polyimides, acrylics, epoxies, photosensitive ceramics, photoresist materials, and combinations thereof. A particularly preferred material for forming sidewalls 18 is a photosensitive polyimide material such as an imidized polyimide (e.g., Amoco 7055), which provides the advantages of excellent insulative properties, high mechanical and thermal stability, and also photosensitivity. The photosensitive property of this polyimide material allows for the precise formation of the sidewalls of the microchannel through standard ultraviolet lithographic patterning techniques.

A first electrically conductive layer 21 is formed on inner surface 15 of substrate 14 between sidewalls 18. A second electrically conductive layer 22 is formed on inner surface 17 of substrate 16 between sidewalls 18 so as to face conductive layer 21. The conductive layers 21 and 22 form electrode plates and are composed of one or more layers of a metallic material such as titanium, gold, palladium, platinum, carbon black, combinations and alloys thereof, and the like. In one embodiment of the invention, the electrode plates are formed from a titanium-aluminum alloy. The conductive layers 21 and 22 define opposing continuous broad boundaries along the length of microchannel 20. When a voltage differential is applied to conductive layers 21 and 22, an electric field is induced across microchannel 20 along the length thereof.

The microchannel 20 can be dimensioned such that the distance d between conductive layers 21 and 22 along the length of microchannel 20 is less than about 100 $\mu$m. Advantageously, microchannel 20 can be dimensioned such that the distance d is about 40 $\mu$m or less, and even about 10

μm or less, because of the micromachining techniques used to fabricate microchannel device 12. The microchannel 20 has a transverse cross-sectional profile that is substantially rectangular, with the width of microchannel 20 substantially greater than the height (or distance p. The microchannel 20 has an aspect ratio of width to height of at least about 20:1, and preferably at least about 80:1. Preferably, the microchannel has a width of about 100 μm to about 5 mm, and a height of about 1 μm to about 40 μm. The large aspect ratios are achieved through micromachining techniques, and provide better resolution in the separation of various particle species.

Figure 3:
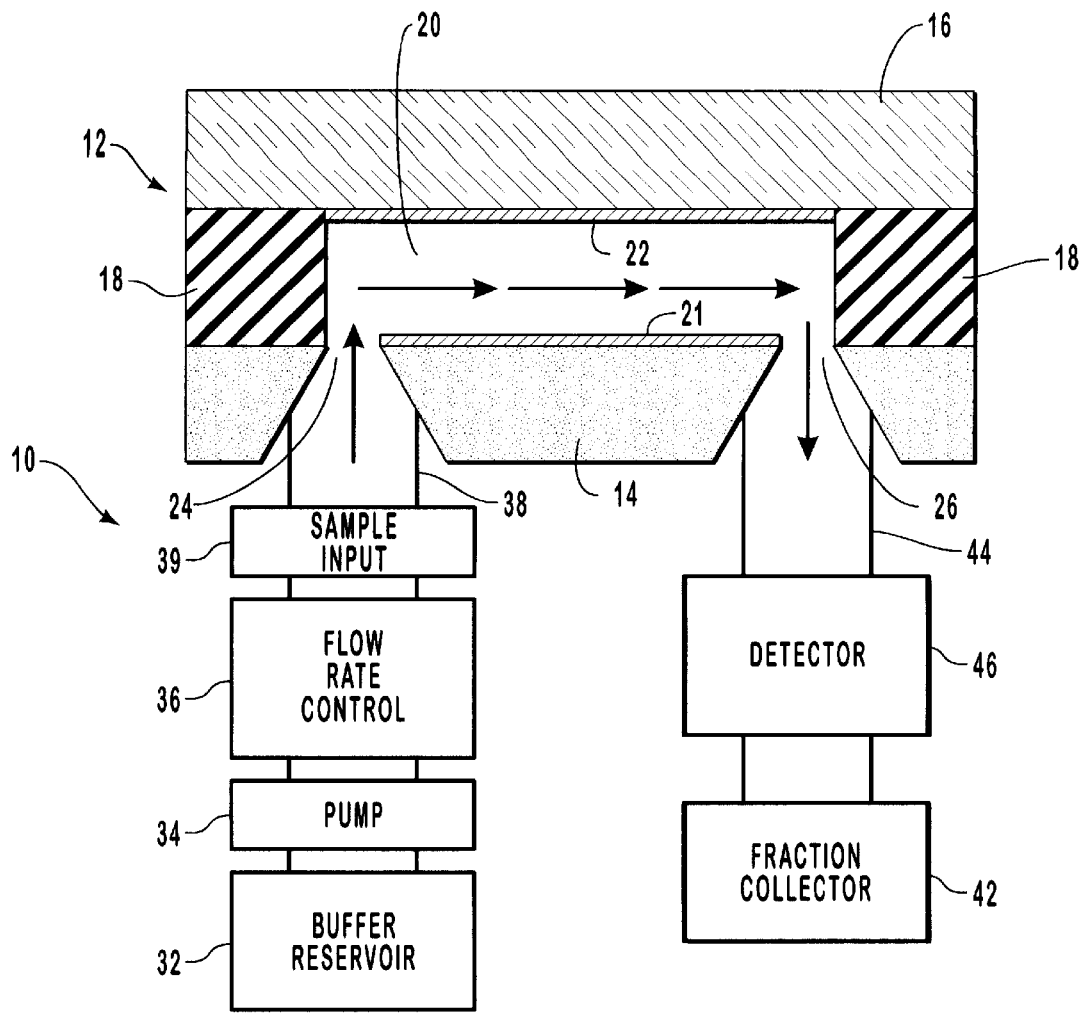
FIG. 3 is a schematic cross-sectional view parallel to fluid flow of the microchannel device of FIG. 2, shown as part of a $\mu$-EFFF system of the present invention.

The microchannel device 12 is shown in FIG. 3 in a schematic cross-sectional view parallel to the flow as part of system 10, with connections to an inlet port 24 and an outlet port 26, both formed in substrate 14. It should be understood that in other embodiments, inlet and outlet ports can be formed in substrate 16, or in both substrates 14 and 16. The inlet port 24 allows fluid flow into microchannel 20, and is in fluid communication with a reservoir means such as a buffer reservoir 32 for holding a fluid such as a carrier buffer solution to be injected into microchannel 20. The buffer solution carries a sample to be analyzed when system 10 is in operation. The reservoir 32 is in fluid communication with a pump 34 such as a syringe pump disposed between reservoir 32 and inlet port 24. A flow rate control device 36 such as a KD Scientific Model 100 can also be disposed between pump 34 and inlet port 24. A fluid communication line 38 such as Teflon tubing interconnects reservoir 32, pump 34, and flow rate control device 36 with inlet port 24. A sample input device 39 is also connected with fluid communication line 38. The sample input device can be a "T" connector with one opening thereof covered with a septum for test sample injection with a syringe.

The outlet port 26 of microchannel device 12 allows fluid flow out of microchannel 20, and can be in fluid communication with a collecting means such as a fraction collector 42 for holding a separated fraction of the analyzed fluid. A fluid communication line 44 such as Teflon tubing interconnects fraction collector 42 with outlet port 26.

The microchannel device 12 is also operatively connected to a detector means such as a detector 46 for analyzing the fluid in microchannel 20. The detector 46 can be incorporated "on-chip" with microchannel device 12 on substrate 14, such as an electrical conductivity or impedance particle detector. For example, the detector can be a conductivity detector that is fabricated directly in the microchannel for detection of particles before they exit the microchannel. Alternatively, the detector 46 can be used "off-chip", such as a conventional optical detector disposed between outlet port 26 and fraction collector 42. Suitable optical detectors include ultraviolet (UV) extinction detectors, light scattering detectors, and the like. The detector is used to monitor the particles separated in microchannel 20 and is preferably interfaced with an output device such as a personal computer (not shown) for subsequent data analysis or a recording device such as a strip chart recorder. The computer can also be used to monitor and record data such as the applied voltage and current in the μ-EFFF system.

Figure 4A:
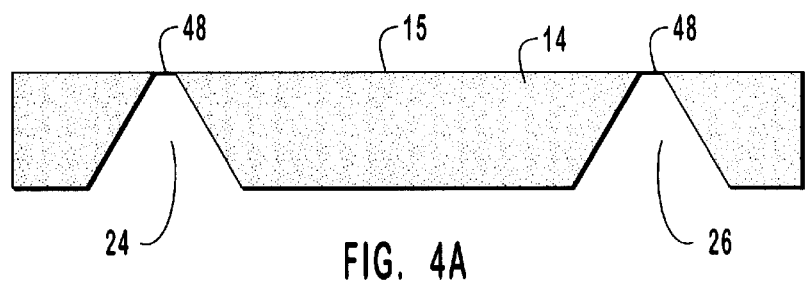
FIGS. 4A–4G show the sequence steps in fabricating a microchannel device according to the present invention.

A method of fabricating a microchannel device used in the μ-EFFF systems of the invention is depicted schematically in FIGS. 4A–4G. As shown in FIG. 4A, a substrate 14 having a substantially planar inner surface 15 is provided, such as a silicon wafer preferably of the <100> crystallographic orientation. The silicon wafer is cleaned according to standard laboratory procedure, such as the RCA cleaning method. A photomask of appropriate dimensions is used to expose and develop through standard photolithographic techniques the patterns on the wafer that will form the inlet and outlet ports. The mask is preferably formed from PECVD (plasma enhanced chemical vapor deposition) deposited silicon nitride laid on the back side of the wafer. Bulk anisotropic etching is used to define inlet port 24 and outlet port 26, which are preferably formed to have a conical shape. The etching process leaves a thin silicon nitride membrane 48 on the front side of substrate 14. The dimensions of inlet and outlet ports 24, 26 can be on the order of about 1 square mm on the backside of the wafer, which narrows to about 400 square μm at the front of the wafer after etching.

Figure 4B:
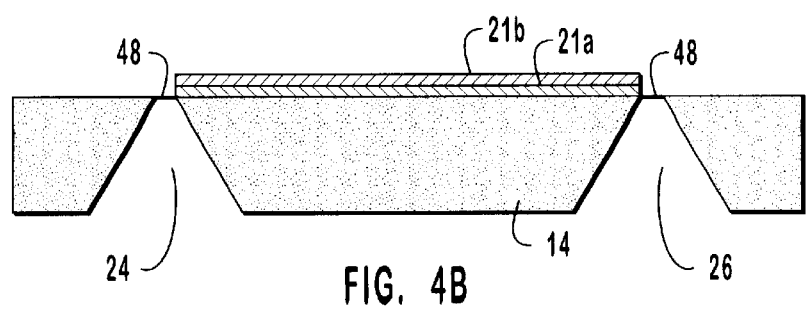

Thin conductive layers 21a and 21b, such as a layer of titanium followed by a layer of gold, are sputtered or evaporated onto inner surface 15 of substrate 14 as depicted in FIG. 4B. The conductive layers 21a and 21b are patterned to form a channel electrode between inlet port 24 and outlet port 26 in the form of an elongated electrode strip.

Figure 4C:
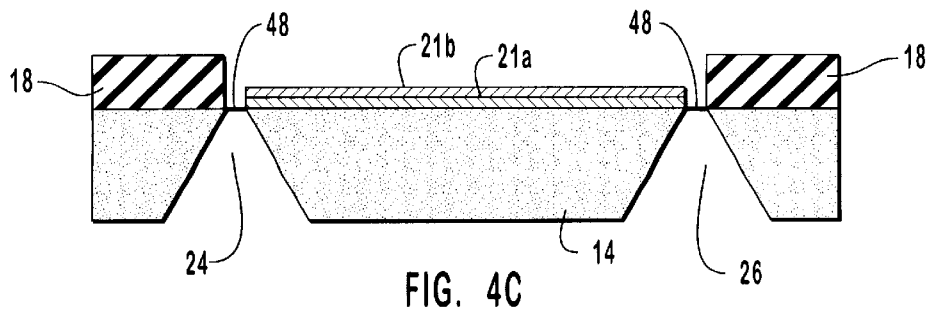

Next, as shown in FIG. 4C, an insulating layer such as a photosensitive polyimide material is deposited on inner surface 15 of substrate 14. The insulating layer is patterned to form opposing sidewalls 18, which will define at least one microchannel, adjacent to conductive layers 21a and 21b. In order to ensure that the polyimide material does not retain any biologically incompatible materials such as unreacted monomers, solvents, and so forth, which might outgas sometime after manufacturing, the polyimide material can be "cured" at a high temperature for a long period of time (typically about 6 hours at a temperature of about 350° C.). Such curing effectively forces any harmful molecules out of the polymer matrix.

Figure 4D:
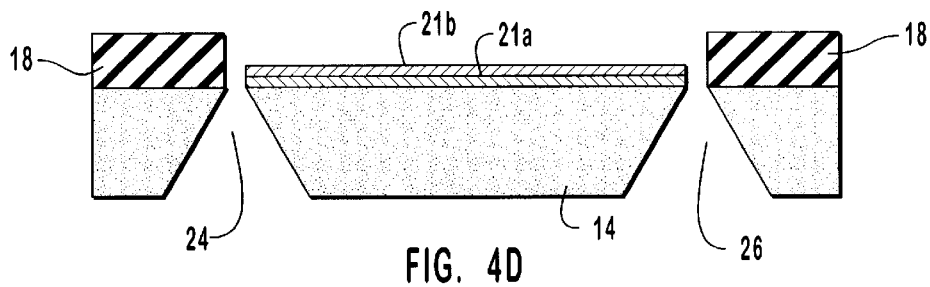
Figure 4E:
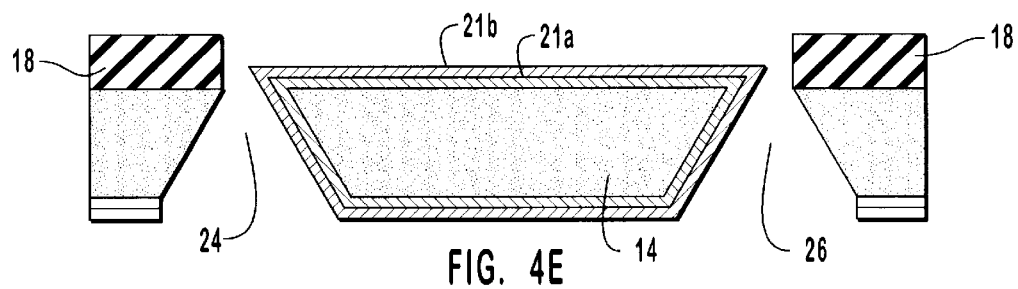

The membrane 48 is then removed from inner surface 15 of substrate 14 by reactive ion etching (RIE), as shown in FIG. 4D. Thereafter, thin conductive layers such as a layer of titanium followed by a layer of gold are sputtered or evaporated onto the backside of substrate 14 as illustrated in FIG. 4E. This provides an electrical connection from conductive layers 21a and 21b to the backside of substrate 14 through inlet and outlet ports 24, 26.

Figure 4F:
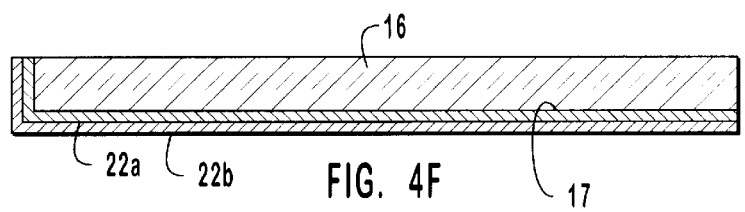

As depicted in FIG. 4F, a substrate 16 having a substantially planar inner surface 17 is provided, such as a glass substrate. Thin conductive layers 22a and 22b, such as a layer of titanium followed by a layer of gold, are sputtered or evaporated onto inner surface 17 of substrate 16. The conductive layers 22a and 22b are patterned to form a channel electrode in the form of an elongated electrode strip.

Figure 4G:
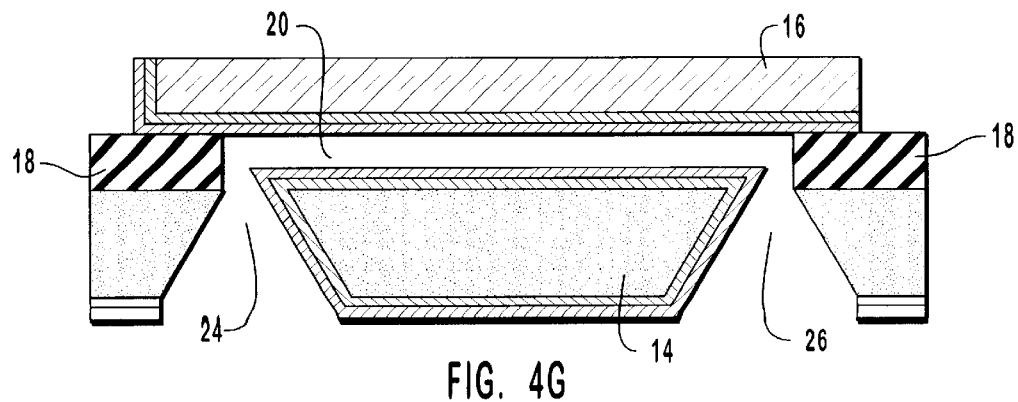

Thereafter, substrate 16 is attached to sidewalls 18 such that the electrodes define opposing continuous boundaries along the length of a microchannel 20, as shown in FIG. 4G. The substrate 16 and sidewalls 18 are preferably bonded together with a UV (ultraviolet) light curable, biocompatible adhesive to complete the structure of the microchannel device. Flanged tubing (not shown) made of Teflon or metal can then be attached to the inlet and outlet ports using a silicone adhesive, in order to provide attachment points for the buffer pumping system for sample injection, and species detection and collection used in the μ-EFFF system.

It should be understood that the above described fabrication process can be used to form microchannel devices with single or multiple microchannels therein. When a microchannel device is formed with a plurality of microchannels therein, a plurality of electrodes are formed on the substrates such that each microchannel is bounded by opposing electrode strips. In addition, a plurality of inlet and outlet ports are formed in one or both substrates for allowing fluid flow into and out of each microchannel. The multiple microchannels are operatively connected to a plurality of detectors, allowing for simultaneous multiple processing of single or multiple test fluids, as discussed in further detail below.

During operation of μ-EFFF system 10, a fluid sample to be analyzed is injected through sample input device 39 into fluid communication line 38 containing a buffering solution from reservoir 32 such as an aqueous buffering solution having a low viscosity. A voltage differential is applied to the electrode plates in microchannel device 12 which induces an electric field across microchannel 22. The applied voltage across the electrode plates is about 0.5 to 3 volts, and preferably less than about 1.7 volts, in order to avoid the detrimental effects of electrolysis. The pump 34 is used to inject a small amount of the fluid sample solution (e.g., 0.1 μL) through inlet port 24 and into microchannel 20. The injected fluid passes through microchannel 20 with the electric field therein, resulting in a separation of particles in the fluid based on charge and particle size. The separated particles are monitored by detector 46 as they pass through outlet port 26. The fluid exiting microchannel 20 can then be directed to fraction collector 42 if desired.

Particle separations can be performed in the μ-EFFF system of the invention by injecting samples as small as 100 nL into the system while the flow is on. After a few seconds (depending on the flow velocity in use to allow the sample to just enter the μ-EFFF channel) the flow is stopped for a short time (e.g., less than about 10 s) to allow the sample in the microchannel to equilibrate. The flow is again started and the separation is then performed. The voltage and current are continuously monitored during the separation to ensure that consistent fields are found in the microchannel.

Figure 5:
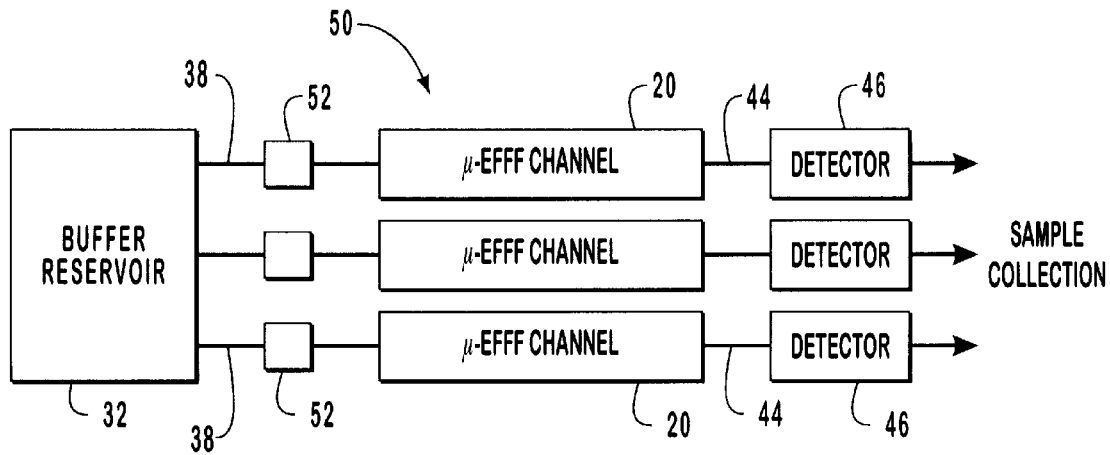
FIG. 5 is a schematic depiction of a $\mu$-EFFF system for parallel analysis according to another embodiment of the present invention.

In other embodiments of the invention, the μ-EFFF system of the invention can be implemented with a plurality of microchannels for parallel or serial analysis of sample fluids. FIG. 5 is a schematic depiction of a parallel system 50 for multiple simultaneous processing of a single type of sample fluid or multiple different sample fluids. The parallel system 50 includes a plurality of microchannels 20, which can be implemented utilizing separate microchannel devices each with one micro channel therein, or with a microchannel device having multiple microchannels therein. While three micro channels are shown in FIG. 5, it should be understood that any number of microchannels can be used together in system 50. For example, from 2 to 100 microchannels can be utilized in system 50.

As shown in FIG. 5, a buffer reservoir 32 is in fluid communication with an input end of each microchannel 20 through a plurality of fluid communication lines 38. Each of the communication lines 38 is connected to a separate sample input device 52 between reservoir 32 and each microchannel. Other devices such as pumps and flow rate control devices may also be connected to communication lines 38. A plurality of fluid communication lines 44 are connected with the output end of each microchannel and direct the fluids exiting the microchannels to a sample collection area. Each microchannel is also operatively connected to a separate detector 46.

Figure 6:
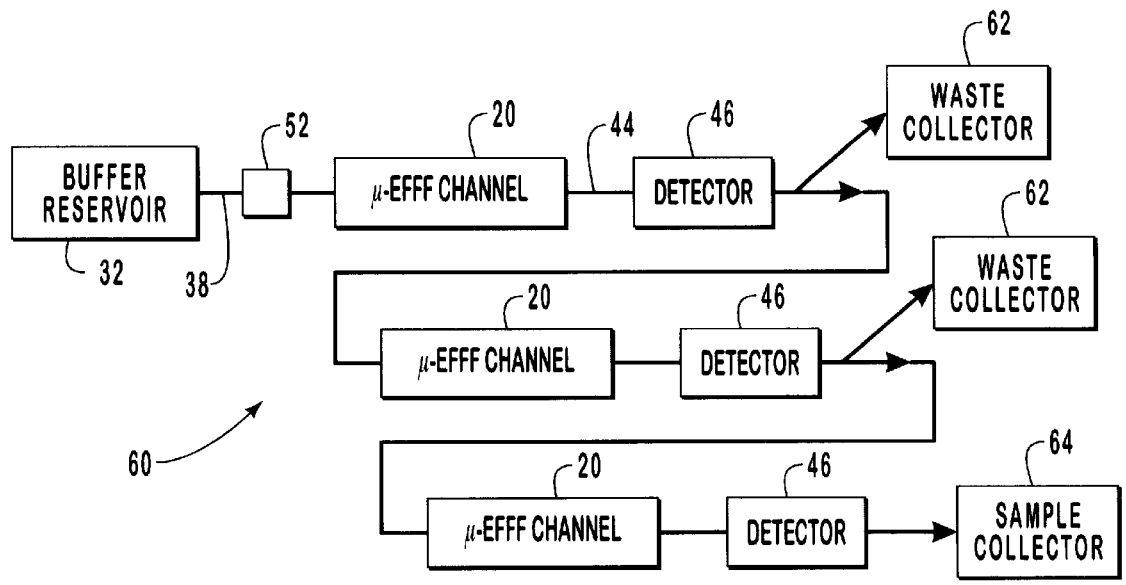
FIG. 6 is a schematic depiction of a $\mu$-EFFF system for serial analysis according to a further embodiment of the present invention.

FIG. 6 shows a serial system 60 for step-wise processing of a sample fluid serially in a purification scheme. The system 60 includes a plurality of microchannel devices, each with a microchannel 20 therein, which are interconnected serially by fluid communication lines. While three microchannels are shown in FIG. 6, it should be understood that any number of microchannels can be interconnected serially in system 60. For example, from 2 to 10 microchannels can be utilized in system 60. Each microchannel 20 is operatively connected to a separate detector 46.

A buffer reservoir 32 is in fluid communication with an input end of a first microchannel through a fluid communication line 38 as depicted in FIG. 6. The communication line 38 is connected to a sample input device 52 between reservoir 32 and the first microchannel. Other devices such as a pump and a flow rate control device may also be connected to communication line 38. A fluid communication line 44 is connected to the output end of the first microchannel. The communication line 44 is capable of directing a portion of the fluid exiting the first microchannel to a waste collector 62, such as by a valve system, while directing the remaining fluid to the input end of a downstream second microchannel for further processing. The system 60 is further configured such that the fluid exiting the second microchannel is directed to a second waste collector 62 and/or to a downstream third microchannel for additional processing. The fluid leaving the third microchannel is directed to a sample collector 64.

The parallel system 50 and serial system 60 operate in a similar manner as described above for system 10, with the additional capabilities of parallel or serial analysis of test sample fluids.

Figure 7:
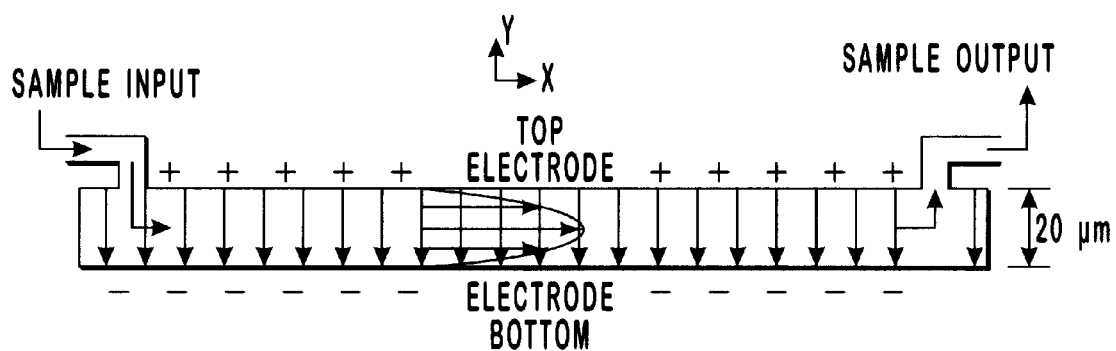
FIG. 7 is a diagram showing the function of a $\mu$-EFFF system of the present invention.
Figure 8:
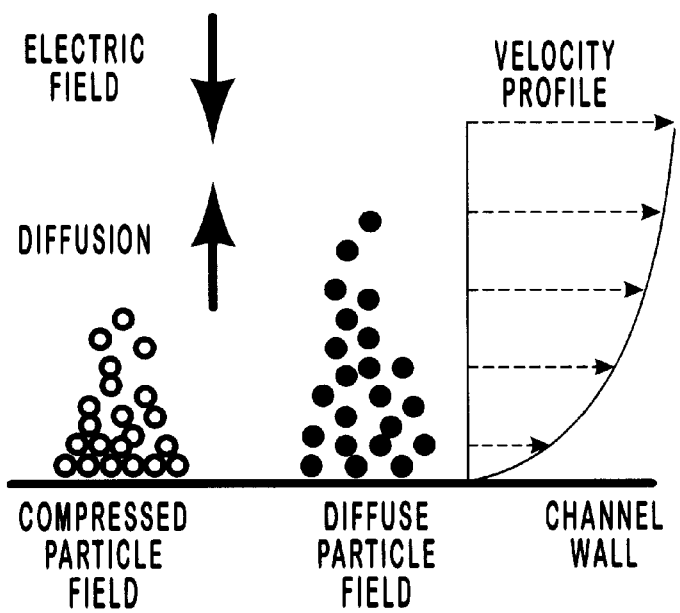
FIG. 8 is a diagram representing the forces internal to a $\mu$-EFFF system of the present invention.

The electric field generated during operation of the μ-EFFF system of the invention is perpendicular to the direction of separation of particles in the fluid flow as depicted in FIG. 7. The electric field controls the relative velocity of particles in the microchannel by forcing the particles towards the microchannel walls. More specifically, the electric field controls the average velocity of the particles in the microchannel by controlling the average distance an exponentially distributed cloud of particles protrudes into the flow stream with respect to the top and bottom electrode surfaces of the microchannel. If the electric field is applied as shown in FIG. 7, a particle cloud with a higher charge density will pack closer to the walls while particles of lower charge density form a more diff-use cloud. The particle cloud with a higher charge density protrudes less into the flow stream and therefore has a lower velocity than particles in the middle of the stream, as depicted graphically in FIG. 8. Since flow in the channel is laminar and therefore parabolic, the particles move through the channel at differential rates based on charge and particle size, thereby separating the particles.

Figure 9:
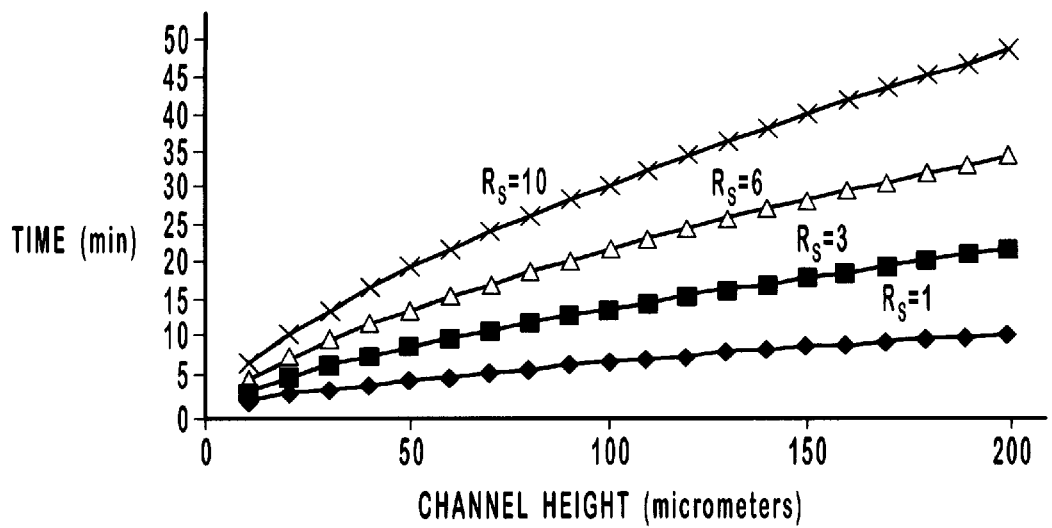
FIG. 9 is a graph showing a theoretical representation of the separation time for selected particles at discrete values of resolution and channel height.

The equation for the resolution, $R_s$ (which is a measure of the ability to distinguish amongst different species of particles), of a μ-EFFF system of the invention is shown in equation (1) below:

$$R_s = \frac{\frac{\Delta d}{d}}{8Dw} \sqrt{\frac{L\mu^3 V_{eff}^3}{6\langle v \rangle}} \tag{1}$$

where $\Delta d$ is the difference between the diameters of the two particles, d is the average diameter of the particles, D is the average diffusion coefficient of the particles, w is the plate separation or channel height, μ is the electrophoretic mobility of the particles, $V_{eff}$ is the effective voltage across the channel, L is the channel length, and <v> is the average buffer flow velocity. FIG. 9 is a graphical representation of equation (1) for 44 and 62 nm particles, showing that the separation time for the particles drops at a given resolution as the channel height decreases.

Examination of equation (1) reveals why the miniaturization of the system of the invention is advantageous. The channel height, w, is inversely proportional to the resolution, indicating that the channel dimension should be minimized. Since all the other parameters are either impossible to change or give undesirable consequences (longer run times or electrolysis), channel height reduction provides a way of improving an EFFF system such as in the present invention. Thus, the thinner the microchannel through which the fluid sample flows, the higher the resolution. It should also be noted from equation (1) that longer channel lengths can also yield enhanced resolution, since the resolution varies as the square root of the length; however, longer channels also result in longer amounts of time to obtain better resolution. A resolution of 1 corresponds to two fully separated peaks (where the term "peak" refers to a measure of the population as a function of position), thereby indicating complete separation of two populations. Values greater than one indicate more than complete separation of the peaks, while values less than one correspond to overlapping peaks.

Another effect encountered in EFFF systems is the steric transition point, where particle elution times begin to reverse once the radius of the particles being separated exceeds a certain length. In normal EFFF modes, smaller particles will elute before larger particles. Beyond the steric transition point, the larger particles will elute before the smaller ones. Since the steric transition point is related to the channel height, miniaturization of the system of the invention impacts the steric transition point. The steric inversion diameter, $d_i$, is given in equation (2) below:

$$d_i = \sqrt{\frac{2kTw}{3\pi\eta\mu V_{eff}}} \quad (2)$$

where k is the Boltzmann constant, T is the absolute temperature, and η is the fluid viscosity.

Important characteristics of any separation system are the peak broadening and resolution of the system, which are both measured in terms of plate heights. The plate height, H, is a measure of variance created by the system while the particles move through the channel. The total plate height is the sum of several contributing factors. One group of factors, known as instrumental factors, $H_i$, can be minimized by good instrument design and operation procedures. A second group of factors are the non-equilibrium effects, $H_n$. These non-equilibrium effects are caused by the natural distribution of the sample over volume elements and the slow movement of particles between volumes. The plate height, H, is given in equation (3) below:

$$H = H_n + H_i \quad (3)$$

$H_n$ can be found using equation (4) if non-polar samples are used.

$$H_n = \frac{1}{105} \frac{w^2 \langle v \rangle}{D} \quad (4)$$

Experimentally, plate heights, H, can be measured and estimates of $H_n$ and $H_i$ can be made. Combining equations 3 and 4, plate heights should increase linearly with flow rate and the y-intercept on the plot is equivalent to the instrumental broadening, $H_i$, which the present invention seeks to minimize.

One area in which miniaturization of the present system is expected to provide improvements is in the area of sample equilibration and the need for stop flow. The establishment of equilibrium in the microchannel is not instantaneous and requires a relaxation time, τ, equal to the time required for a particle to migrate from one electrode to the other in the presence of the applied electric field. The relaxation time, τ, can be found using equation (5) below:

$$\tau = \frac{w^2}{2\mu V_{eff}} \quad (5)$$

where w is the spacing between electrodes, $V_{eff}$ is the effective voltage across the channel, and μ is the electrophoretic mobility of the species of particle.

The μ-EFFF system of the invention is effective in separating various species of molecules or particulates in solution with very small sample sizes efficiently, quickly, and inexpensively, and with a high degree of resolution, while allowing for reduced separation times. In addition, the μ-EFFF system allows for greater resolution in the separation of molecular species and permits smaller sample sizes to be analyzed at faster rates than what has been achieved in prior systems.

The micromachining techniques used to fabricate the microchannel device used in the μ-EFFF system allow for simple and precise construction of the flow channels utilizing biocompatible materials. The micromachining techniques used to fabricate the microchannel device allow for increased manufacturing precision, with an increase in resolution by decreasing the channel thickness. In addition, the ability to precisely define the channel and electrodes improves resolution by reducing band broadening. The batch fabrication methods inherent in micromachining technologies also allow for the design of disposable μ-EFFF systems eliminating the need for cleaning the systems after every use.

The μ-EFFF system of the invention can be utilized in many different applications. For example, the system can be used in the collection of fractions, and has the ability to perform separations of cells and organelles, large molecules, large molecular complexes, colloids, emulsions, liposomes and other particulate vehicles. Other applications include quick and accurate separations of macromolecules, environmental water monitoring, tests for sample contamination, and sample pretreatment.

The following examples are given to illustrate the present invention, and are not intended to limit the scope of the invention.

EXAMPLE 1

Microchannel devices for use in μ-EFFF systems were fabricated by the following procedure. A 3 inch (76 mm) single-side polished silicon wafer (<100> crystallographic orientation) was put into a PE-CVD apparatus and a layer of silicon nitride having a thickness of 2500 Å was deposited on the polished side of the wafer. The silicon nitride was then patterned using photoresist as a mask on both sides of the wafer. Patterning was done such that 1 mm square openings were made in the silicon nitride on the unpolished side of the wafer in a $CF_4$ plasma. Bulk anisotropic etching was then performed in a 20% KOH solution at a temperature of 56° C. for a period of 24 hours to define the inlet and outlet ports. The KOH etching process left a thin silicon nitride membrane about 1000–2000 Å thick on the front polished side of the wafer. The openings on the polished side of the wafer were about 400 square μm.

Next, a layer of 1000 Å of titanium followed by a layer of 1500 Å of gold were sputtered onto the polished side of the wafer. These metals were then patterned to form a first channel electrode using a photoresist mask and an etchant mixture of 400 g of KI, 100 g of $I_2$, and 400 ml water, in order to etch the gold; and also a 1% HF solution to etch the titanium. Thick photosensitive polyimide micromolding (Amoco Ultradel 7505) was used to define the micro flow channels (10–40 µm in height). The polyimide was spun onto the wafers and then placed onto a leveling plate for 15 minutes to ensure an even coating and to eliminate any potential thickness irregularities. After ultraviolet exposure and pattern development according to standard laboratory procedures, the polyimide was completely cured in an oven at a temperature of 350° C. for 6 hours.

The thin silicon nitride membrane was then removed using reactive ion etching (RIE) in a $CF_4$ plasma. A 1000 Å layer of titanium and a 1500 Å layer of gold were then sputtered onto the unpolished side of the wafer. This provided electrical contact between the front side electrodes and the backside of the wafer through the ports. A 1000 Å layer of titanium and a 1500 Å layer of gold were then sputtered onto a glass substrate that had been cut to fit over a group of the microsized channels. The titanium and gold layers on the glass substrate were subsequently patterned to form the second channel electrode.

The glass and silicon substrates were then bonded together using a UV curable, biocompatible adhesive (3341 Medical Device Adhesive from Loctite). The glass substrate was pressed against the silicon substrate with the electrodes aligned, while the UV adhesive was dispensed near the polyimide-glass interface and allowed to flow between the substrates due to capillary action. Once the adhesive had completely surrounded the channel, it was cured using a UV lamp. A conductive adhesive was then used to bond a wire to a contact pad on the glass substrate, thereby allowing a lead to be attached. Steel tubing with an inner diameter of 125 µm was attached to the silicon substrate over the inlet and outlet ports using a ferrule bonded to the silicon substrate. The microchannel devices fabricated in accordance with the process described hereinabove had channels 4–6 cm in length, 20–30 µm in height, and 0.4–8 mm in width, with aspect ratios between 20 and 400.

EXAMPLE 2

In order to perform separations using the microchannel devices fabricated according to the procedure described in Example 1, one entrance of a "T" connector is attached to the steel tubing on the silicon substrate. Another entrance of the T connector is covered with a septum for sample input. The sample is injected through the septum and into the T connector using a 10 µL Hamilton syringe containing the sample plug. The other opening on the T connector is linked to a syringe pump using 10 cm of Teflon tubing with an outer diameter of 0.8 mm, and an inner diameter of 350 µm. The output port is connected to a detector such as a Linear UV-106 absorbance detector (capable of monitoring extinction at 254 nm) by using 3 cm of 350 µm inner diameter Teflon tubing. The fluid output from the detector can be connected to a fraction collector if desired. The detector is electrically connected to a recording device (e.g., a PC or strip chart recorder) which collects the data output from the detector and monitors the measured current and applied voltage. The power to the top and bottom electrodes in the channels is provided by a standard power supply, such as the Hewlett Packard 6128C DC Power Supply.

EXAMPLE 3

The microchannel devices fabricated according to the procedure described in Example 1 were tested for mechanical integrity of the microchannels by forcing fluids through the microchannels and checking for leaks. It was found that the microchannels can withstand fluid velocities as high as 4 cm/sec, while still maintaining mechanical integrity. Normal operating flows are typically about 1 cm/sec or lower.

EXAMPLE 4

A photosensitive polyimide material for use in the microchannel device of the invention was tested for potential swelling. The photosensitive polyimide material was spun on 6 silicon wafers at a series of thicknesses (estimated). The polyimide material was patterned in the same manner as for the µ-EFFF devices described in Example 1, and was cured for 24 hours at 285° C. The cured polyimide was then soaked in deionized water for 24 hours at room temperature. The results of this test are shown in Table 1 below.

TABLE 1

| Polyimide Test | | | | |
|---|---|---|---|---|
| Uncured (µm) | Cured (µm) | Shrinkage | Soaked in $H_2O$ (µm) | Swelling |
| 9.1 | 5.0 | 45% | 5.0 | 0% |
| 16.3 | 11.5 | 30% | 11.9 | 3.0% |
| 27.5 | 15.5 | 44% | 15.9 | 2.9% |
| 57 | 28.0 | 51% | 28.4 | 1.4% |
| 60 | 29.0 | 52% | 30.0 | 3.4% |
| 66 | 34.5 | 48% | 35.3 | 2.3% |
| Average | — | 45% | — | 2.2% |

Examination of Table 1 reveals that polyimide swelling in water is potentially significant. Since the channel thickness or height is of critical importance in µ-EFFF systems, a variation in channel thickness can have a ripple effect through the system and cause results that vary from the expected. Nevertheless, the 2.2% average swelling is small enough not to cause significant differences, especially when considering that the amount of swelling in the actual devices will be much less. Only the polyimide that makes up the sidewalls of the microchannel will be exposed to the buffer solution in the µ-EFFF devices. Thus, a much smaller surface area of the polyimide is exposed to the buffer solution in the µ-EFFF devices than in this test, and swelling of the polyimide is unlikely to significantly affect the operation of the µ-EFFF devices.

EXAMPLE 5

Since separations of cells and cellular components is of interest for the device of the invention, hemolysis testing was performed using the µ-EFFF devices, the photosensitive polyimide, and the silicone used in the interface design. The testing involved placing 2 g of crushed µ-EFFF devices (about ½ a 3 in (76 mm) wafer) into a test tube with 10 ml of a phosphate buffer solution (PBS) (8.5 g NaCl+0.2 g $NaH_2PO_4H_2O$+0.47 g $Na_2HPO_4$[anhydrous] in 1 L $H_2O$, adjusted to pH 7.4 with NaOH). Also, 2 g samples of cured polyimide and silicone rubber were run separately to determine if there was any hemolysis caused by these materials in a higher concentration. A positive (detergent) and negative (glass) control were also prepared in a similar manner.

Sheep blood samples were prepared by placing 0.5 mL of blood in a 5 mL test tube and adding PBS until the tube was about a third full. A blood sample for each test was prepared in this manner. Each sample was centrifuged three times at low speed until the cells were separated. The supernatant was drawn off after each spin down with additional PBS being added between each spin down to wash the cells. After the final run in the centrifuge, 0.2 mL of blood cells were taken and added to each of the material samples prepared earlier.

Each of the mixtures was then incubated in a water bath at 37° C. for 1 hour. The supernatant was then drawn from each sample and 5 mL test tubes were filled about ¾ full. The supernatant was then centrifuged at high speed for about 5 minutes or until the blood cell bodies were completely removed. The amount of absorbance at 520 nm for each sample was then measured using a spectrophotometer that was zeroed using a blank (PBS in test tube). The percent hemolysis for each sample was then calculated by dividing the difference between the test sample and the negative control by the difference between the positive control and the negative control. The results of the test are shown in Table 2 below.

TABLE 2

Hemolysis Test

| Sample | Absorbance | % Hemolysis |
|---|---|---|
| Detergent (+ Control) | 1.35 | 100 |
| Glass (− Control) | 0.025 | 0 |
| Crushed μ-EFFF devices | 0.025 | 0 |
| Polyimide | 0.01 | 0 |
| Silicone Rubber | 0.04 | 1.14 |

Examining the test results in Table 2, it can be seen that very little, if any, hemolysis had taken place, since the measured absorbance for all samples of interest was very close to the negative control. Therefore, it appears that the materials chosen are effective for use in separating cells and cellular components, at least in the area of cell lysis.

EXAMPLE 6

The parameters for a conventional macro-EFFF system compared to the parameters of a μ-EFFF system of the invention are listed in Table 3 below.

TABLE 3

| Parameter | macro-EFFF | μ-EFFF |
|---|---|---|
| Channel length | 37 cm | 4–6 cm |
| Channel height | 127 μm | 1–30 μm |
| Aspect ratio | 100 | up to 400 |
| Relaxation time | 45 sec | 1.5 sec |
| Measured number of plates | 925 | 150 |
| Theoretical plates | 31,000 | 31,200 |
| Sample size | 5 μL | 0.1 μL |
| Parallel channels | none | 10 |
| Run times | 60 min. | 15 min. |
| Field strengths at 1.7 V | 95 V/cm | 850 V/cm |

It should be noted that great improvements have been made in the μ-EFFF system in terms of system size, aspect ratio, relaxation time, sample size, run times, and parallel operation. The reduction in system size allows for the possibility of portable EFFF systems and a decrease in the laboratory space required by conventional systems. The increased aspect ratio should lessen the impact of edge effects in the system and thereby reduce plate heights. The reduction in relaxation times and run times should speed analysis in the laboratory. The reduction in sample sizes alleviates the need to greatly multiply a sample before analysis (as is done in DNA amplification by polymerase chain reaction (PCR)), or reduces the effort needed to collect a sample large enough for analysis. The parallel channels allow for multiple tests to be run at the same time.

EXAMPLE 7

Microchannel devices for use in μ-EFFF systems were fabricated by similar procedures as described in Example 1, with the following changes. Most of the changes in fabrication were designed to reduce peak broadening in the system. First, the size of the inlet ports was reduced to 200 square μm. Second, the electrical connection was not made through the inlet and outlet ports, but rather the metallization that comprised the electrodes was extended to the edge of the silicon wafer where the connection was then made. Third, angled input and output flow regions were added to the microchannel. Fourth, a conductive adhesive was used to bond a wire directly to the wafer in the area of the electrode metallization to allow electrical contact. Fifth, the interface between the macro and micro fluid regimes was altered. A plastic ferrule from Upchurch Scientific was affixed using a UV curable adhesive to the surface of the silicon wafer directly over the inlet and outlet ports in order to localize the 125 μm inner diameter steel tubing bonded in place over the ports. The microchannel devices were 5.4 cm in length, 6 mm in width, and with a electrode plate separation distance of 28 μm. This allowed a sample volume of up to 9.072 μL.

Figure 10:
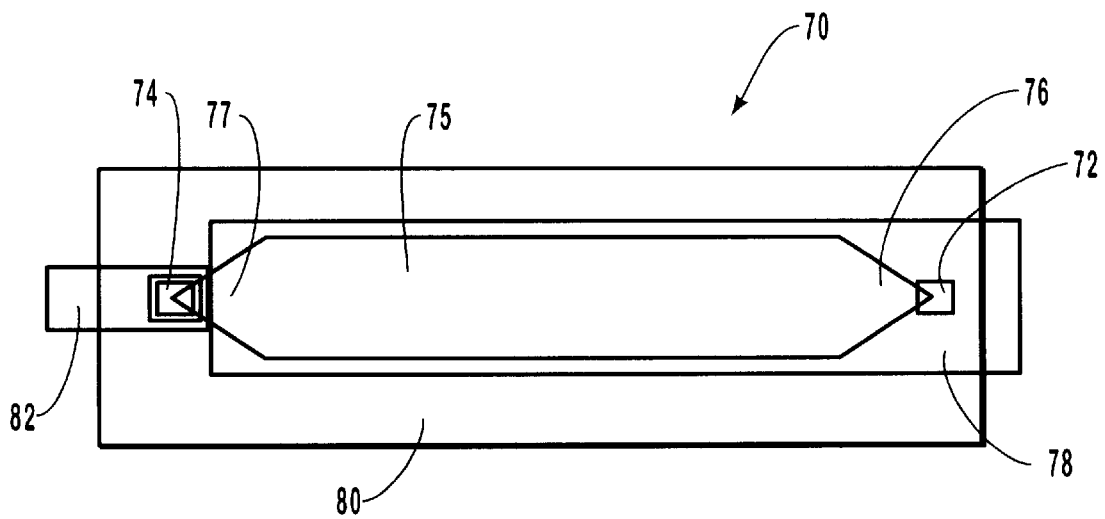
FIG. 10 is a schematic depiction of a microchannel device according to another embodiment of the present invention which utilizes an on-chip detector.

The layout of a microchannel device 70 made according to the procedures of Example 7 is shown schematically in FIG. 10. The device 70 includes an inlet port 72 and an outlet port 74, both in fluid communication with a microchannel 75 which narrows at each respective end toward the ports, forming an angled input flow region 76 and an angled output flow region 77. A channel electrode 78 forms a broad boundary of microchannel 75. An insulative layer 80 surrounds microchannel 75, forming a narrow boundary therearound. A detector electrode 82 is operatively connected to a detector adjacent to outlet port 74 in an on-chip configuration.

The dead volume in the connections to the microchannel was reduced to 7.7 μL by narrowing the microchannel toward the inlet and outlet ports. At a flow rate of 1 mL/hr (0.174 cm/s in the microchannel) this reduces the delay to 27 seconds in the microchannel.

Figure 11:
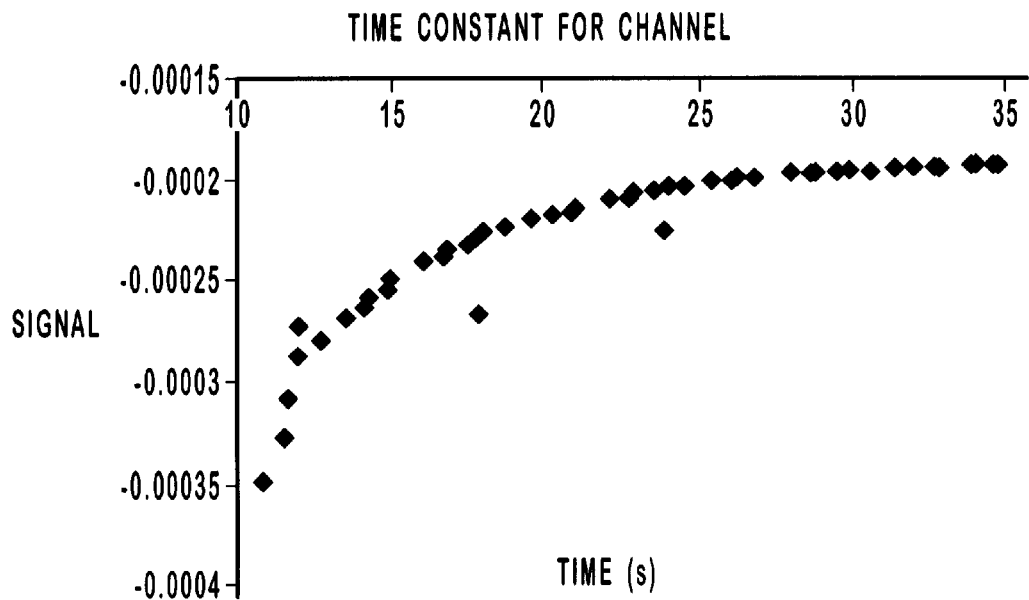
FIG. 11 is a graph showing the results of a voltage step test for a $\mu$-EFFF system of the present invention.

The time constant for changes in the electric current in the microchannel and by association the internal electric field was measured using a voltage step test, the results of which are shown in the graph of FIG. 11. The data from this test indicates that the time constant for the channel is about 4 seconds, or an order of magnitude less than for prior macro-EFFF systems.

EXAMPLE 8

Both on-chip and off-chip detectors were demonstrated and compared with respect to μ-EFFF system performance for microchannel devices made according to the procedures of Example 7. The off-chip detector was a UV detector monitoring at a wavelength of 254 nm. The on-chip detector was a conductivity detector that was fabricated directly in the channel for detection of particles before they exit the EFFF channel. The detector included two parallel wires on the glass and silicon wafer surfaces that were fabricated in the same manner as the channel electrodes. Electrical connection to the detector was made as described in Example 7 for the channel electrodes. The conductivity detector operated by applying a constant 5 V across the microchannel then measuring the current in the circuit.

Plate height measurements were made by injecting 100 nL samples of acetone into the μ-EFFF system for a series of flow rates. The band broadening calculations were performed using equations (3) and (4) described above, and the results were plotted to determine the instrumental component of the plate height. Of particular interest is the difference in band broadening between the system with the on-chip detector and the off-chip detector.

Figure 12:
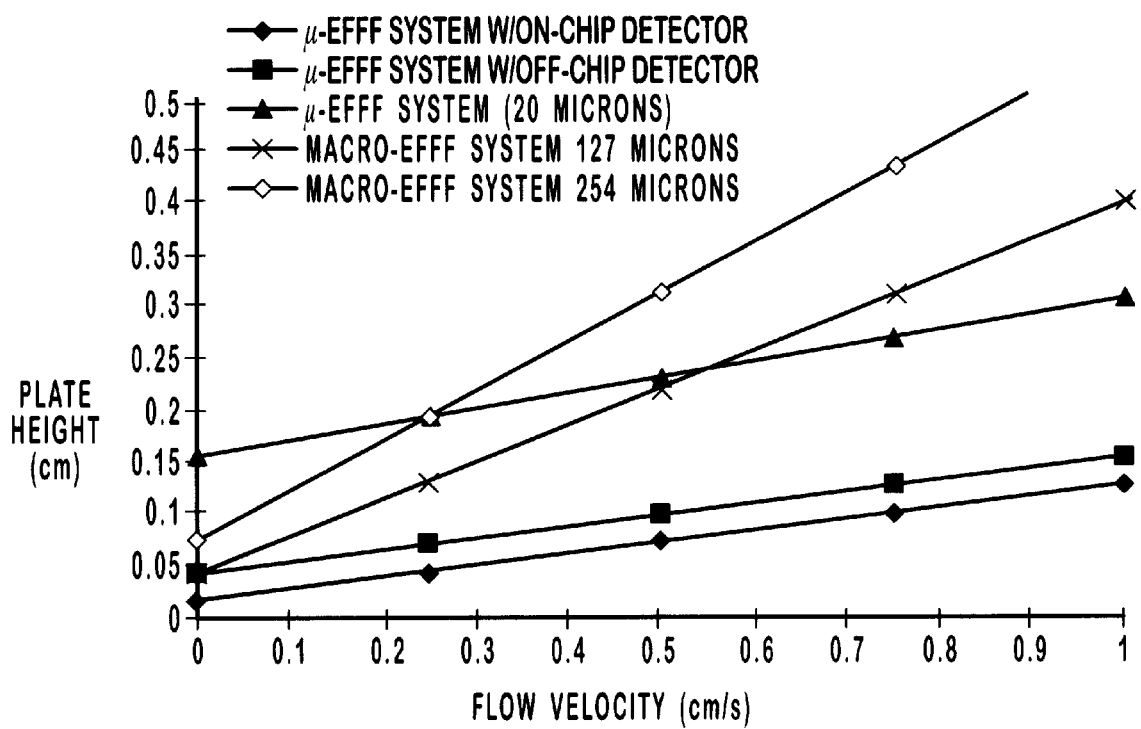
FIG. 12 is a graph showing the results of band broadening calculations for various conventional macro systems and $\mu$-EFFF systems of the present invention.

The results of band broadening calculations for the $\mu$-EFFF systems are shown in the graph of FIG. 12 for the system with an on-chip detector and the system with an off-chip detector. For comparison, the results are shown with typical band broadening calculations for current macro-EFFF systems (127 and 254 microns), and for a $\mu$-EFFF system (20 microns) without the angled input and output flow regions in the microchannel. FIG. 12 shows that thinner channels produce smaller peak broadening only if the instrumental band broadening is small. The instrumental band broadening is indicated by the y-intercept on the graph. It should be noted that great improvements were made in band broadening by using microchannel devices with angled input and output flow regions (providing an improved macro-to-micro interface) and by using an on-chip detector. As shown in the graph of FIG. 12, there was a three-fold improvement using the system with an off-chip detector, and a five-fold improvement using the system with an on-chip detector, compared to the 20 micron $\mu$-EFFF system without angled flow regions.

Figure 13:
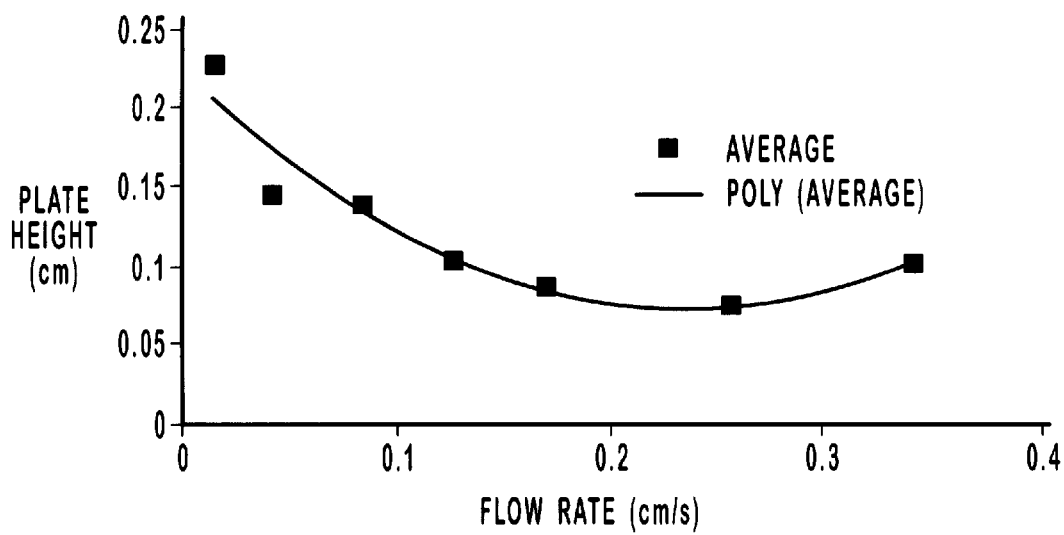
FIG. 13 is a graph showing the peak broadening measurements of a $\mu$-EFFF system with an off-chip detector.

One effect not shown in the graph of FIG. 12 is the influence that diffusion has on peak broadening in the off-chip detector. The graph of FIG. 13 shows the peak broadening measurements of a $\mu$-EFFF system with the off-chip detector. The increasing values for low flow rates indicate that diffusion is beginning to dominate at the low flow rates. Since this effect disappears with the on-chip detector, it is apparent that the diffusion must occur in the detector itself. The reason for the change in the relative importance of diffusion is due to the large dimensions found in the off-chip detector compared to the channel itself.

EXAMPLE 9

Figure 14:
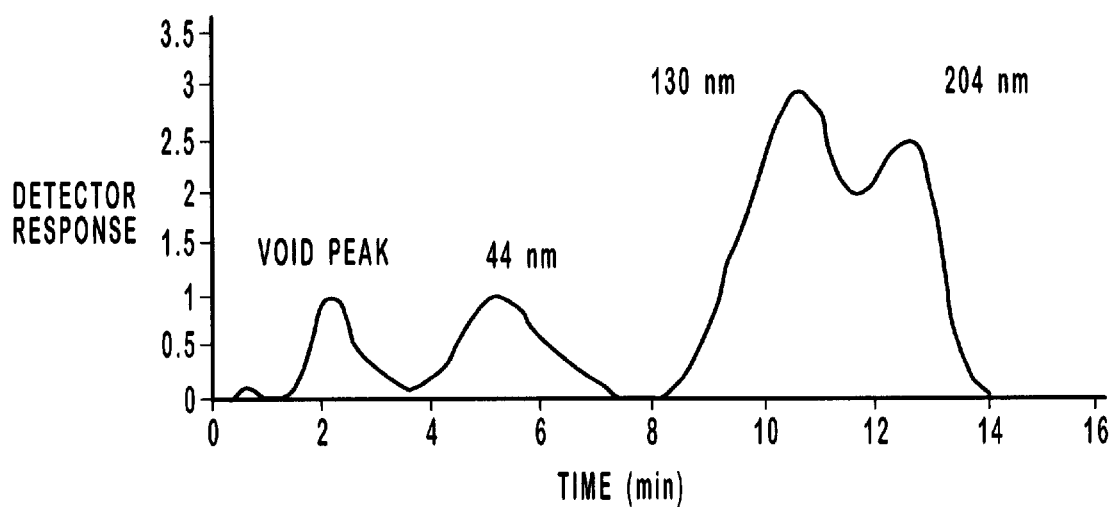
FIG. 14 is a graph showing the results of a separation using a $\mu$-EFFF system with an off-chip detector.

A separation run was performed using a $\mu$-EFFF system with an off-chip detector. The run was performed using a 0.1 $\mu$L mixture of 44, 130, and 204 nm polystyrene particles (from Seradyn). The parameters of the system included an applied voltage of 1.9 V, a current of 170 $\mu$A, a flow velocity of 0.06 mL/hr, a buffer solution of deionized water, a channel length of 6 cm, and a channel height of 28 $\mu$m. A 10 second relaxation period was used after allowing 30 seconds for the sample plug to reach the $\mu$-EFFF channel. The resolution results of the separation run are shown graphically in FIG. 14. The elution times were about 5–6 minutes for the 44 nm particles, about 10–11 minutes for the 130 nm particles, and about 12–13 minutes for the 204 nm particles. The graph shows that all of the particles were separated from the void peak and from each other. It should be noted that a resolution similar to this in conventional macro systems would take about 1 hour.

EXAMPLE 10

Figure 15:
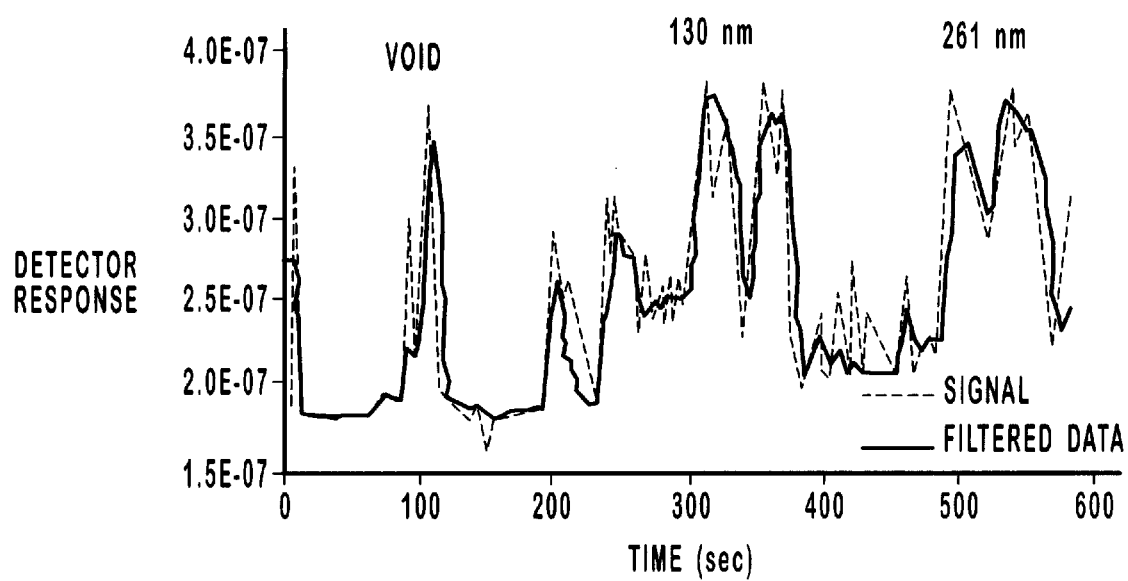
FIG. 15 is a graph showing the results of a separation using a $\mu$-EFFF system with an on-chip detector.

A separation run was performed using a $\mu$-EFFF system having similar parameters as the system of Example 9, except that an on-chip detector was utilized. The run was performed using a 0.1 $\mu$L mixture of 130 and 261 nm polystyrene particles. The resolution results of the separation run are shown graphically in FIG. 15. There was about a 50% reduction in run time compared to the system with the off-chip detector in Example 9. While there was significant noise in the unfiltered signal, sharp peaks are shown in the graph of FIG. 15, indicating the void peak and the various particles. The resolution of the system of Example 10 is 5 times that of the separation made by the system of Example 9. Thus, the on-chip detector can provide a higher performance, lower cost replacement for bulky and expensive off-chip detectors.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A microchannel device for electrical field-flow fractionation of a fluid, comprising:
   a first substrate having a substantially planar inner surface;
   a first electrically conductive layer on the inner surface of the first substrate;
   a second substrate having a substantially planar inner surface and positioned over the first substrate;
   a second electrically conductive layer on the inner surface of the second substrate and facing the first electrically conductive layer;
   an intermediate layer interposed between the first substrate and the second substrate, the intermediate layer patterned so as to form opposing sidewalls of a microchannel, with the first and second electrically conductive layers defining opposing continuous boundaries along the length of the microchannel, wherein the microchannel is dimensioned such that the distance between the first and second electrically conductive layers along the length of the microchannel is less than about 100 $\mu$m;
   an inlet port in the first or second substrate for allowing fluid flow into the microchannel;
   an outlet port in the first or second substrate for allowing fluid flow out of the microchannel; and
   one or more detectors in operative communication with the microchannel for analyzing a fluid in or from the microchannel, the detectors selected from one or more of the group consisting of electrical conductivity detectors and impedance detectors.

2. The microchannel device of claim 1, wherein the first substrate comprises a material selected from the group consisting of silicon, glass, plastics, metals, and combinations thereof.

3. The microchannel device of claim 1, wherein the second substrate comprises a material selected from the group consisting of silicon, glass, plastics, metals, and combinations thereof.

4. The microchannel device of claim 1, wherein the first and second electrically conductive layers comprise metallic materials selected from the group consisting of titanium, gold, carbon black, palladium, platinum, and combinations or alloys thereof.

5. The microchannel device of claim 1, wherein the intermediate layer comprises an insulating material selected from the group consisting of a photosensitive polyimide, photosensitive ceramics, acrylics, epoxies, photoresist, and combinations thereof.

6. The microchannel device of claim 1, wherein the microchannel has an aspect ratio of width to height of about 20:1 or greater.

7. The microchannel device of claim 1, wherein the microchannel has an aspect ratio of width to height of about 80:1 or greater.

8. The microchannel device of claim 1, wherein the microchannel is dimensioned such that the distance between the first and second electrically conductive layers along the length of the microchannel is about 40 $\mu$m or less.

9. The microchannel device of claim 1, wherein the microchannel is dimensioned such that the distance between the first and second electrically conductive layers along the length of the microchannel is about 10 $\mu$m or less.

10. The microchannel device of claim 1, wherein the microchannel has a transverse cross-sectional profile that is substantially rectangular.

11. The microchannel device of claim 1, wherein the first and second electrically conductive layers comprise electrodes that are capable of inducing an electric field across the microchannel when a voltage differential is applied to the electrodes.

12. A microchannel device for electrical field-flow fractionation of a fluid, comprising:
a first substrate having a substantially planar inner surface;
a first plurality of electrodes on the inner surface of the first substrate;
a second substrate having a substantially planar inner surface and positioned over the first substrate;
a second plurality of electrodes on the inner surface of the second substrate and facing the first plurality of electrodes;
an intermediate layer interposed between the first substrate and the second substrate, the intermediate layer patterned so as to form opposing sidewalls of a plurality of microchannels, with the first and second plurality of electrodes each defining opposing continuous boundaries along the lengths of the microchannels, wherein the microchannels are dimensioned such that the distance between the first and second plurality of electrodes along the lengths of the microchannels is less than about 100 $\mu$m;
a plurality of inlet ports in the first or second substrate for allowing fluid flow into the microchannels;
a plurality of outlet ports in the first or second substrate for allowing fluid flow out of the microchannels; and
a plurality of detectors in operative communication with the microchannels for analyzing fluids in or from the microchannels, the detectors selected from one or more of the group consisting of electrical conductivity detectors and impedance detectors.

13. The microchannel device of claim 12, wherein the first substrate comprises a material selected from the group consisting of silicon, glass, plastics, metals, and combinations thereof.

14. The microchannel device of claim 12, wherein the second substrate comprises a material selected from the group consisting of silicon, glass, plastics, metals, and combinations thereof.

15. The microchannel device of claim 12, wherein the first and second plurality of electrodes comprise metallic materials selected from the group consisting of titanium, gold, carbon black, palladium, platinum, and combinations or alloys thereof.

16. The microchannel device of claim 12, wherein the intermediate layer comprises an insulating material selected from the group consisting of a photosensitive polyimide, photosensitive ceramics, acrylics, epoxies, photoresist, and combinations thereof.

17. The microchannel device of claim 12, wherein the microchannels have an aspect ratio of width to height of about 20:1 or greater.

18. The microchannel device of claim 12, wherein the microchannels have an aspect ratio of width to height of about 80:1 or greater.

19. The microchannel device of claim 12, wherein the microchannels are dimensioned such that the distance between the first and second plurality of electrodes along the lengths of the microchannels is about 40 $\mu$m or less.

20. The microchannel device of claim 12, wherein the microchannels are dimensioned such that the distance between the first and second plurality of electrodes along the lengths of the microchannels is about 10 $\mu$m or less.

21. The microchannel device of claim 12, wherein the microchannels have a transverse cross-sectional profile that is substantially rectangular.

22. The microchannel device of claim 12, wherein the first and second plurality of electrodes are capable of inducing an electric field across the microchannels when a voltage differential is applied to the electrodes.

23. A micromachined system for electrical field-flow fractionation of a fluid, comprising:
a first microchannel device comprising:
a first substrate having a substantially planar inner surface;
at least one first electrode on the inner surface of the first substrate;
a second substrate having a substantially planar inner surface and positioned over the first substrate;
at least one second electrode on the inner surface of the second substrate and facing the first electrode; and
an insulating intermediate layer interposed between the first substrate and the second substrate, the intermediate layer patterned so as to form opposing sidewalls of at least one microchannel, with the first and second electrodes defining opposing continuous boundaries along the length of the microchannel, wherein the microchannel is dimensioned such that the distance between the first and second electrodes along the length of the microchannel is less than about 100 $\mu$m;
an inlet port in the first or second substrate for allowing fluid flow into the microchannel; and
an outlet port in the first or second substrate for allowing fluid flow out of the microchannel;
a reservoir means in fluid communication with the inlet port, for holding a fluid to be injected into the microchannel; and
a first detector operatively connected with the first microchannel device for analyzing a fluid in the microchannel, wherein the first detector is an electrical conductivity detector or an impedance detector.

24. The system of claim 23, wherein the intermediate layer comprises a material selected from the group consisting of a photosensitive polyimide, photosensitive ceramics, acrylics, epoxies, photoresist, and combinations thereof.

25. The system of claim 23, wherein the microchannel has an aspect ratio of width to height of about 20:1 or greater.

26. The system of claim 23, wherein the microchannel is dimensioned such that the distance between the first and second electrodes along the length of the microchannel is about 40 $\mu$m or less.

27. The system of claim 23, wherein the reservoir means is in fluid communication with a pump, a sample input device, and a flow control device, each of which is disposed between the reservoir means and the inlet port.

28. The system of claim 23, wherein the first detector is adjacent to the outlet port.

29. The system of claim 23, further comprising at least one additional microchannel device implemented with the first microchannel device for multiple parallel processing of single or multiple test fluids.

30. The system of claim 23, further comprising a second microchannel device in downstream fluid communication with the first microchannel device, the second microchannel device comprising the same components as the first microchannel device.

31. The system of claim 30, further comprising a second detector operatively connected to the second microchannel device.

32. The system of claim 30, further comprising a third microchannel device in downstream fluid communication with the second microchannel device, the third microchannel device comprising the same components as the first microchannel device.

33. The system of claim 32, further comprising a third detector operatively connected to the third microchannel device.

34. A micromachined system for electrical field-flow fractionation of a fluid, comprising:
- a first substrate having a substantially planar inner surface;
- a first plurality of electrodes on the inner surface of the first substrate;
- a second substrate having a substantially planar inner surface and positioned over the first substrate;
- a second plurality of electrodes on the inner surface of the second substrate and facing the first plurality of electrodes;
- an intermediate layer interposed between the first substrate and the second substrate, the intermediate layer patterned so as to form opposing sidewalls of a plurality of microchannels, with the first and second plurality of electrodes each defining opposing continuous boundaries along the lengths of the microchannels, wherein the microchannels are dimensioned such that the distance between the first and second plurality of electrodes along the lengths of the microchannels is less than about 100 $\mu$m;
- a plurality of inlet ports in the first or second substrate for allowing fluid flow into the microchannels;
- a plurality of outlet ports in the first or second substrate for allowing fluid flow out of the microchannels;
- a buffer reservoir in fluid communication with the inlet ports; and
- a plurality of detectors operatively connected with the microchannels for multiple parallel processing of single or multiple test fluids in the microchannels, wherein the detectors are selected from one or more of the group consisting of electrical conductivity detectors, and impedance detectors.

35. The system of claim 34, wherein the intermediate layer comprises a material selected from the group consisting of a photosensitive polyimide, photosensitive ceramics, acrylics, epoxies, photoresist, and combinations thereof.

36. The system of claim 34, wherein the microchannels have an aspect ratio of width to height of about 20:1 or greater.

37. The system of claim 34, wherein the microchannels are dimensioned such that the distance between the first and second electrodes along the lengths of the microchannels is about 40 $\mu$m or less.

38. The system of claim 34, wherein the reservoir is in fluid communication with a plurality of pumps, sample input devices, and flow control devices, each of which is disposed between the reservoir and the plurality of inlet ports.

39. The system of claim 34, wherein the detectors are adjacent to the outlet ports.

40. A method of fabricating a microchannel device for electrical field-flow fractionation of a fluid, comprising the steps of:
- providing a first substrate having a substantially planar inner surface;
- providing a second substrate having a substantially planar inner surface;
- forming at least one inlet port and at least one outlet port in the first or second substrates;
- forming at least one first electrode layer on the inner surface of the first substrate;
- forming at least one second electrode layer on the inner surface of the second substrate;
- forming an insulating layer on the inner surface of the first substrate such that the insulating layer forms opposing sidewalls of at least one microchannel adjacent to the first electrode layer;
- attaching the second substrate to the insulating layer such that each of the first and second electrode layers define opposing continuous boundaries along the length of the microchannel, the distance between the first and second electrode layers along the length of the microchannel being less than about 100 $\mu$m; and
- forming a detector in the microchannel, the detector configured to analyze a fluid in the microchannel.

41. The method of claim 40, wherein the inlet and outlet ports are formed by etching conically-shaped openings in the first substrate.

42. The method of claim 40, wherein the first electrode layer is formed by sputtering and patterning a metallic material on the inner surface of the first substrate to form an elongated electrode strip.

43. The method of claim 40, wherein the second electrode layer is formed by sputtering and patterning a metallic material on the inner surface of the second substrate to form an elongated electrode strip.

44. The method of claim 40, wherein the insulating layer is formed by depositing and patterning a material selected from the group consisting of a photosensitive polyimide, photosensitive ceramics, acrylics, epoxies, photoresist, and combinations thereof.

45. The method of claim 40, wherein the second substrate is attached to the insulating layer with a biocompatible, ultraviolet light curable adhesive.

46. The method of claim 40, wherein the microchannel device is fabricated to have a plurality of microchannels therein.

47. The method of claim 40, wherein the detector formed in the microchannel is an electrical conductivity detector or an impedance detector.

48. An electrical field-flow fractionation process, comprising the steps of:
- providing a first microchannel device comprising:
  - a first substrate having a substantially planar inner surface;
  - at least one first electrode on the inner surface of the first substrate;
  - a second substrate having a substantially planar inner surface and positioned over the first substrate;
  - at least one second electrode on the inner surface of the second substrate and facing the first electrode; and an insulating intermediate layer interposed between the first substrate and the second substrate, the intermediate layer patterned so as to form opposing sidewalls of at least one microchannel, with the first and second electrodes defining opposing continuous boundaries along the length of the microchannel, wherein the microchannel is dimensioned such that the distance between the first and second electrodes along the length of the microchannel is less than about 100 µm;

applying a voltage differential to the first and second electrodes in order to induce an electric field across the microchannel;

injecting a fluid through an inlet port in one of the substrates and into the microchannel;

passing the fluid through the microchannel with the electric field therein in order to separate particles in the fluid; and monitoring the separated particles in the fluid with a first detector selected from the group consisting of an electrical conductivity detector and an impedance detector.

49. The process of claim 48, wherein the first microchannel device includes a plurality of microchannels therein for multiple parallel processing of single or multiple test fluids.

50. The process of claim 48, further comprising the step of providing at least one additional microchannel device implemented with the first microchannel device for multiple parallel processing of single or multiple test fluids.

51. The process of claim 48, further comprising the step of directing a portion of the fluid from the outlet port to a fraction collector.

52. The process of claim 48, further comprising the step of directing a portion of the fluid from the outlet port to a waste collector, and directing the remaining portion of the fluid to a second microchannel device for further separation of particles in the fluid, the second microchannel device comprising the same components as the first microchannel device.

53. The process of claim 52, further comprising the step of monitoring the separated particles in the second microchannel device with a second detector.

54. The process of claim 52, further comprising the step of directing a portion of the fluid from the second microchannel device to a waste collector, and directing the remaining portion of the fluid to a third microchannel device for further separation of particles in the fluid, the third microchannel device comprising the same components as the first microchannel device.

55. The process of claim 54, further comprising the step of monitoring the separated particles in the third microchannel device with a third detector.

56. The process of claim 54, further comprising the step of directing the fluid from the third microchannel device to a sample collector.

* * * * *